United States Patent
Müller et al.

(10) Patent No.: US 10,717,997 B2
(45) Date of Patent: Jul. 21, 2020

(54) METHOD FOR STORING GASEOUS HYDROGEN THROUGH PRODUCING METHANOATE (FORMATE)

(71) Applicant: Johann Wolfgang Goethe-Universität, Frankfurt am Main (DE)

(72) Inventors: Volker Müller, Frankfurt (DE); Kai Schuchmann, Weiterstadt (DE)

(73) Assignee: JOHANN WOLFGANG GOETHE-UNIVERSITÄT, Frankfurt am Main (DE)

( * ) Notice: Subject to any disclaimer, the term of this patent is extended or adjusted under 35 U.S.C. 154(b) by 0 days.

(21) Appl. No.: 16/018,736

(22) Filed: Jun. 26, 2018

(65) Prior Publication Data

US 2018/0320207 A1 Nov. 8, 2018

Related U.S. Application Data

(62) Division of application No. 14/890,301, filed as application No. PCT/EP2014/062892 on Jun. 18, 2014, now Pat. No. 10,036,045.

(30) Foreign Application Priority Data

Jun. 18, 2013 (EP) .................... 13172411

(51) Int. Cl.
*C12P 7/62* (2006.01)
*C12P 7/40* (2006.01)
*B01D 53/62* (2006.01)

(52) U.S. Cl.
CPC ............... *C12P 7/62* (2013.01); *B01D 53/62* (2013.01); *C12P 7/40* (2013.01); *B01D 2251/95* (2013.01); *B01D 2257/502* (2013.01)

(58) Field of Classification Search
None
See application file for complete search history.

(56) References Cited

U.S. PATENT DOCUMENTS

2015/0079650 A1\* 3/2015 Koepke ............ C12Y 102/0700
435/158

OTHER PUBLICATIONS

Alissandraros, A. et al., "Formate production through biocatalysis." Bioengineered, 2013, 4 (5): 348-350.
Beller, M., Bornscheuer, U. T., "CO2 Fixation through Hydrogenation by Chemical or Enzymatic Methods." Angew. Chem. Int. Ed., 2014, 53: 4527-4528.
Boddien, A. et al., "CO2-"Neutral" Hydrogen Storage Based on Bicarbonates and Formates\*\*." Angew. Chem. Int. Ed., 2011, 50: 6411-6414.
Hull, J. F. et al., "Reversible hydrogen storage using CO2 and a proton-switchable iridium catalyst in aqueous media under mild temperatures and pressures." Nature Chemistry, May 2012, 4: 383-388.
Laurenczy, G., "Hydrogen Storage and Delivery: the Carbon Dioxide—Formic Acid Couple." Chimia, 2011, 65: 663-666.
Parkin, A. et al., "Rapid and Efficient Electrocatalytic CO2/CO Interconversions by Carboxydothermus hydrogenoformans CO Dehydrogenase I on an Electrode." J. Am. Chem. Soc., 2007, 129: 10328-10329.
Preraira, I. A. C., "An Enzymatic Route to H2 Storage" Science, Dec. 2013, 342: 1329-1330.
Peters. V. et al., "Transient Production of Formate During Chemolithotrophic Growth of Anaerobic Microorganisms on Hydrogen." Current Microbiology, 1999, 38: 285-289.
Poehlein, A. et al., "An Ancient Pathway Combining Carbon Dioxide Fixation with the Generation and Utilization of a Sodium Ion Gradient for ATP Synthesis." PLoS ONE, Mar. 2012, 7 (3): 1-8.
Reda, T. et al., "Reversible interconversion of carbon dioxide and formate by an electroactive enzyme." PNAS, Aug. 1008, 105(31): 10654-10658.
Schuchmann, K, Muller, V., "A Bacterial Electron-bifurcating Hydrogenase\*." Journal of Biological Chemistry, Sep. 2012, 287 (37): 31165-31171.
Schuchmann, K, Müller, V., "Direct and Reversible Hydrogenation of CO2 to Formate by a Bacterial Carbon Dioxide Reductase." Science, Dec. 2013, 342: 1382-1385.
Schuchmann, K. et al., "An electron bifurcating hydrogenase in the acetogenic bacterium *Acetobacterium woodii*." Gordon Research Conferences, Lewiston, Maine, U.S.A., 2012, pp. 1-5.
Straub, M., "Fermentative Acetatproduktion durch Homoacetat-Garung bzw. Acetacetatbildung," Dissertation/Thesis Universitat Ulm, Ulm, Germany, 2012, pp. 86 and 102.

\* cited by examiner

*Primary Examiner* — Anand U Desai
(74) *Attorney, Agent, or Firm* — Saliwanchik, Lloyd & Eisenschenk (57) ABSTRACT

The present invention relates to a method for storing gaseous hydrogen, comprising the steps of producing methanoate (formate) through contacting gaseous hydrogen with carbon dioxide in the presence of a hydrogen dependent carbon dioxide reductase (HDCR), and thereby storing of said gaseous hydrogen. The HDCR and/or its complex is preferably derived from *Acetobacterium woodii*.

15 Claims, 2 Drawing Sheets

Specification includes a Sequence Listing.

```
                         SEQUENCE LISTING

<160> NUMBER OF SEQ ID NOS: 8

<210> SEQ ID NO 1
<211> LENGTH: 724
<212> TYPE: PRT
<213> ORGANISM: Acetobacterium woodii

<400> SEQUENCE: 1

Met Lys Lys Val Leu Thr Thr Cys Pro Tyr Cys Gly Ser Gly Cys
1               5                   10                  15

Gln Leu Tyr Leu Asn Val Glu Asp Gly Lys Ile Val Ser Ala Thr Pro
                20                  25                  30

Ala Asp Gly Arg Thr Asn Gln Glu Thr Leu Cys Leu Lys Gly His Tyr
            35                  40                  45

Gly Trp Asp Tyr Leu Asn Asp Pro Gln Ile Leu Thr Lys Arg Leu Thr
    50                  55                  60

Lys Pro Gln Ile Arg Lys Asn Gly Lys Leu Glu Asp Val Glu Trp Asp
65                  70                  75                  80

Glu Ala Ile Ser Tyr Thr Ala Gln Arg Leu Ser Glu Ile Lys Thr Lys
                85                  90                  95

Tyr Gly Ser Asp Ser Ile Ile Gly Thr Gly Cys Ala Arg Gly Ser Gly
                100                 105                 110

Asn Glu Ala Asn Tyr Val Met Gln Lys Phe Met Arg Ala Val Ile Gly
            115                 120                 125

Thr Asn Asn Val Asp His Cys Ala Arg Val Cys His Ala Pro Ser Val
    130                 135                 140

Ser Gly Leu Ala Tyr Ser Leu Gly Ser Gly Ala Met Ser Leu Ser Ile
145                 150                 155                 160

Pro Glu Ile Glu Asp Ala Lys Leu Leu Leu Ile Phe Gly Tyr Asn Pro
                165                 170                 175

Ala Glu Ser His Pro Ile Val Ala Arg Arg Ile Ile Lys Ala Lys Gln
            180                 185                 190

Lys Gly Ala Lys Ile Ile Val Val Asp Pro Arg Ile Thr Glu Ser Ala
        195                 200                 205

Arg Ile Ala Asp Leu His Leu Gln Ile Lys Gly Gly Ser Asn Leu Ala
    210                 215                 220

Leu Val Gln Ala Met Ala Asn Val Ile Ile Leu Glu Gly Leu Val Asp
225                 230                 235                 240

His Pro Phe Ile Glu Asp His Thr Ser Gly Tyr Glu Glu Tyr Lys Lys
                245                 250                 255

Gln Ile Glu Lys Tyr Pro Pro Glu Tyr Ala Gln Ser Ile Cys His Ile
            260                 265                 270

Pro Ala Asp Thr Ile Arg Gln Ala Ala Arg Gln Tyr Ala Lys Ala Asp
        275                 280                 285
```

-continued

```
Ser Ala Ala Ile Leu Trp Gly Met Gly Val Thr Gln Phe Gly Gln Ala
    290                 295                 300

Val Asp Val Val Lys Gly Leu Ala Ser Leu Ala Leu Leu Thr Gly Asn
305                 310                 315                 320

Phe Gly Gly Pro Ser Met Gly Val Gly Pro Val Arg Gly Gln Asn Asn
                325                 330                 335

Val Gln Gly Gly Cys Asp Met Gly Ala Leu Pro Asn Cys Tyr Pro Gly
                340                 345                 350

Tyr Gln Asp Val Thr Asp Ile Ile Arg Glu Lys Phe Glu Lys Ala
            355                 360                 365

Trp Gly Val Arg Leu Ser Lys Lys Asn Gly Ile Pro Leu Thr Gln Val
    370                 375                 380

Pro Gln Tyr Val Leu His Glu Lys Asp Glu Lys Lys Ile Arg Ala
385                 390                 395                 400

Tyr Tyr Ile Phe Gly Glu Asp Pro Gly Gln Ser Asp Pro Asp Leu Asn
                405                 410                 415

Asp Met Arg Lys Ala Leu Asp Ala Leu Glu Phe Val Val Gln Asp
            420                 425                 430

Ile Tyr Met Asn Lys Thr Gly Leu Lys Ala Asp Val Ile Leu Pro Ala
                435                 440                 445

Thr Ala Trp Gly Glu His Glu Gly Val Cys Thr Cys Ala Asp Arg Gly
    450                 455                 460

Phe Gln Arg Ile Arg Lys Ala Val Glu Pro Lys Gly Asp Leu Lys Pro
465                 470                 475                 480

Asp Trp Glu Ile Ile Ser Leu Val Ser Thr Ala Met Gly Tyr Pro Met
                485                 490                 495

Ser Tyr Lys Asn Thr Lys Glu Ile Trp Asp Glu Met Arg Ser Leu Ser
            500                 505                 510

Pro Leu Phe Phe Gly Ala Thr Tyr Glu Lys Ile Glu Lys Met Gly Gly
    515                 520                 525

Val Leu Trp Pro Cys Lys Asp Glu Ser Met Ala Asp Lys Gly Thr Met
530                 535                 540

Tyr Leu His Lys Asp Gly Val Phe Ala His Leu Asp Gly Lys Gly Lys
545                 550                 555                 560

Phe Phe Ala Thr Glu Trp Arg Ala Pro Gly Glu Ile Glu Ser Lys Glu
                565                 570                 575

Tyr Pro Phe Ser Leu Ser Thr Val Arg Glu Val Gly His Tyr Ser Val
            580                 585                 590

Arg Thr Met Thr Gly Asn Cys Arg Thr Leu Ser Asn Leu Glu Asp Glu
    595                 600                 605

Pro Gly Trp Ile Gln Met Ser Leu Phe Asp Cys Glu Lys Leu Lys Val
    610                 615                 620

Lys Glu Gly Asp Leu Ile Arg Val Ser Ser Lys Arg Gly Thr Ile
625                 630                 635                 640

Thr Arg Val Lys Pro Thr Glu Arg Val Lys Ala Gly Ala Thr Tyr Met
                645                 650                 655

Thr Tyr Gln Trp Trp Val Gly Ala Cys Asn Asp Leu Thr Val Pro Tyr
            660                 665                 670

Leu Asp Pro Val Ser Asn Thr Pro Glu Ser Lys Tyr Cys Ala Ile Lys
            675                 680                 685

Leu Glu Lys Ile Asp Asp Gln Val Trp Ala Glu Lys Tyr Ile Arg Glu
    690                 695                 700
```

```
Ser Tyr Gln Asn Ile Arg Arg Asp Met Gly Ile Asp Ile Val Glu Lys
705                 710                 715                 720

Glu Tyr Arg Leu

<210> SEQ ID NO 2
<211> LENGTH: 177
<212> TYPE: PRT
<213> ORGANISM: Acetobacterium woodii

<400> SEQUENCE: 2

Met Asn Tyr Phe Val Lys Gly Asn Pro Asp Leu Cys Ile Gly Cys Arg
1               5                   10                  15

Thr Cys Met Ile Ser Cys Val Ile Ala His Glu Gly Glu Lys Ile Phe
            20                  25                  30

Gln Met Asn Pro Gly Glu Tyr Val Phe Asn Pro Lys Leu Asp Ile Val
        35                  40                  45

Lys Thr Ala Thr Ile Thr Val Pro Val Gln Cys Lys His Cys Glu Asn
50                  55                  60

Pro Ala Cys Met Asn Val Cys Pro Val Lys Ala Ile Lys Ile Ile Gly
65                  70                  75                  80

Cys Ala Val Val Val Thr Pro Asp Lys Cys Ile Gly Cys Lys Thr Cys
                85                  90                  95

Met Ile Ala Cys Pro Tyr Gly Ala Ile Asn Met Ile Lys Ser Ser Asp
            100                 105                 110

Gly Lys Lys Gln Ile Asp Asn Ser Glu Arg Met Val Ala Asn Lys Cys
        115                 120                 125

Asp Leu Cys Val Gly Arg Glu Ala Gly Pro Ala Cys Ile Gln Val Cys
130                 135                 140

Pro Thr Ala Ser Leu Lys Leu Val Thr Gln Glu Asp Val Glu Ser Ala
145                 150                 155                 160

Ile Ser Ser Lys Arg Ile Ala Ala Ala Val Ser Leu Tyr Gln Val Lys
                165                 170                 175

Asp

<210> SEQ ID NO 3
<211> LENGTH: 722
<212> TYPE: PRT
<213> ORGANISM: Acetobacterium woodii
<220> FEATURE:
<221> NAME/KEY: misc_feature
<222> LOCATION: (139)..(139)
<223> OTHER INFORMATION: Xaa is Selenocystein

<400> SEQUENCE: 3

Met Glu Lys Gln Val Leu Thr Thr Cys Ala Tyr Cys Gly Ala Gly Cys
1               5                   10                  15

Gln Leu Tyr Leu Asn Val Asn Asp Gly Lys Ile Val Asn Ala Thr Pro
            20                  25                  30

Ala Pro Gly Arg Thr Asn Glu Glu Thr Leu Cys Leu Lys Gly Arg Tyr
        35                  40                  45

Gly Trp Asp Phe Leu Asn Asp Pro Gln Ile Leu Thr Lys Arg Leu Thr
    50                  55                  60

Lys Pro Gln Ile Arg Lys Asn Gly Leu Leu Glu Val Glu Trp Asp
65                  70                  75                  80

Glu Ala Ile Ser Tyr Thr Ala Gly Arg Leu Ser Glu Ile Lys Ala Lys
                85                  90                  95

Tyr Gly Pro Asp Ser Ile Met Gly Thr Gly Ser Ala Arg Gly Pro Gly
```

```
                100                 105                 110
Asn Glu Ala Asn Tyr Ile Met Gln Lys Phe Met Arg Ala Ala Ile Gly
            115                 120                 125
Thr Asn Asn Val Asp His Cys Ala Arg Val Xaa His Ala Pro Ser Val
        130                 135                 140
Ala Gly Leu Gln Tyr Ser Leu Gly Ser Gly Ala Met Ser Met Gly Val
145                 150                 155                 160
Pro Glu Ile Glu Asp Ala Lys Leu Leu Phe Ile Phe Gly Tyr Asn Gly
                165                 170                 175
Ala Asp Ser His Pro Ile Val Ala Arg Arg Ile Val Lys Ala Lys Gln
            180                 185                 190
Lys Gly Ala Lys Ile Ile Val Thr Asp Pro Arg Ile Thr Glu Ser Ala
        195                 200                 205
Arg Ile Ala Asp Ile His Leu Gln Leu Lys Gly Gly Ser Asn Met Ala
210                 215                 220
Leu Val Asn Ala Ile Gly Asn Val Ile Ile Asn Glu Gly Leu Ala Asp
225                 230                 235                 240
Gln Lys Phe Ile Glu Asp His Thr Ser Gly Tyr Glu Glu Tyr Lys Glu
                245                 250                 255
Ile Val Ala Lys Tyr Thr Pro Glu Tyr Ala Glu Val Ile Cys His Val
            260                 265                 270
Pro Ala Gln Leu Ile Arg Glu Ala Ala Arg Ala Tyr Ala Lys Ala Glu
        275                 280                 285
Thr Ser Met Ile Leu Tyr Gly Met Gly Val Cys Gln Phe Ala Gln Ala
    290                 295                 300
Val Asp Val Val Lys Gly Leu Ala Ser Leu Ala Leu Leu Thr Gly Asn
305                 310                 315                 320
Phe Gly Gly Pro Ser Met Gly Ile Gly Pro Val Arg Gly Gln Asn Asn
                325                 330                 335
Val Gln Gly Ala Cys Asp Met Gly Ala Leu Pro Asn Cys Tyr Pro Gly
            340                 345                 350
Tyr Gln Ser Val Thr Asp Asp Ala Val Arg Glu Lys Phe Glu Lys Ala
        355                 360                 365
Trp Gly Val Pro Leu Ser Asn Lys Val Gly Ile Pro Leu Thr His Val
    370                 375                 380
Pro His Arg Val Leu Glu Glu Lys Asp Glu Ala Lys Lys Ile His Ala
385                 390                 395                 400
Tyr Tyr Ile Phe Gly Glu Asp Pro Ala Gln Ser Asp Pro Asp Leu Ala
                405                 410                 415
Glu Ile Arg Glu Thr Leu Glu Lys Val Asp Phe Val Val Gln Asp
            420                 425                 430
Ile Phe Met Asn Lys Thr Gly Leu Gln Ala Asp Val Ile Leu Pro Ser
        435                 440                 445
Thr Ser Trp Gly Glu His Glu Gly Ile Tyr Thr Ala Cys Asp Arg Gly
    450                 455                 460
Phe Gln Arg Ile Arg Lys Ala Ile Glu Pro Lys Gly Asp Val Lys Thr
465                 470                 475                 480
Asp Trp Glu Ile Ile Ser Leu Ile Ser Thr Ala Met Gly Tyr Pro Met
                485                 490                 495
His Tyr Gln Asn Thr Lys Glu Ile Trp Asp Glu Met Arg His Leu Thr
            500                 505                 510
Pro Ser Phe Lys Gly Ala Thr Tyr Glu Lys Ile Glu Ala Leu Gly Gly
        515                 520                 525
```

```
Val Gln Trp Pro Cys Arg Asp Glu Ser Met Asp Asp Lys Gly Thr Gln
            530                 535                 540
Tyr Leu His Lys Gly Gly Lys Phe Ala His Pro Asp Gly Arg Ala Lys
545                 550                 555                 560
Phe Phe Ser Ala Glu Trp Arg Pro Pro Cys Glu Val Glu Ser Pro Glu
                565                 570                 575
Tyr Pro Phe Ser Leu Ser Thr Val Arg Glu Val Gly His Tyr Ser Val
                580                 585                 590
Arg Thr Met Thr Gly Asn Cys Arg Ala Leu Ala Asn Leu Glu Asp Glu
            595                 600                 605
Pro Gly Trp Ile Gln Met Ser Pro Ala Asp Cys Thr Lys Leu Lys Val
            610                 615                 620
Lys Glu Gly Asp Leu Ile Arg Val Tyr Ser Lys Arg Gly Ser Leu Ile
625                 630                 635                 640
Thr Arg Val Leu Pro Thr Glu Arg Val Lys Ala Gly Ala Thr Tyr Met
                645                 650                 655
Thr Tyr Gln Trp Trp Ile Gly Ala Cys Asn Glu Leu Thr Thr Pro Tyr
                660                 665                 670
Leu Asp Pro Val Ser Asn Thr Pro Glu Ser Lys Tyr Cys Ala Ile Asn
            675                 680                 685
Leu Glu Lys Ile Asp Asp Gln Asp Trp Ala Glu Lys Phe Val Lys Asp
            690                 695                 700
Ser Tyr Glu Arg Ile Arg Thr Asn Met Gly Ile Asp Thr Ala Lys Lys
705                 710                 715                 720
Gly Val

<210> SEQ ID NO 4
<211> LENGTH: 176
<212> TYPE: PRT
<213> ORGANISM: Acetobacterium woodii

<400> SEQUENCE: 4

Met Asn Tyr Phe Val Lys Gly Asn Pro Asp Leu Cys Ile Gly Cys Arg
1               5                   10                  15
Thr Cys Met Ile Gly Cys Val Ile Ala His Glu Gly Glu Lys Ile Phe
            20                  25                  30
Gln Met Asn Pro Gly Glu Tyr Val Phe Asn Pro Lys Leu Asp Ile Val
        35                  40                  45
Lys Thr Ala Thr Ile Thr Val Pro Val Gln Cys Lys His Cys Glu Asn
    50                  55                  60
Pro Ala Cys Met Asn Val Cys Pro Val Lys Ala Ile Glu Ile Ile Asp
65                  70                  75                  80
Asn Ala Val Val Ile Asn Gln Asp Lys Cys Ile Gly Cys Lys Thr Cys
                85                  90                  95
Met Ile Ala Cys Pro Tyr Gly Ala Val Asp Met Val Val Ser Ser Asp
                100                 105                 110
Gly Lys Lys Gln Thr Asp Asp Ser Asp Arg Ile Val Ala Asn Lys Cys
            115                 120                 125
Asp Leu Cys Ala Gly Ile Glu Gly Gly Pro Thr Cys Ile Arg Val Cys
        130                 135                 140
Pro Thr Ala Ala Leu Lys Leu Val Thr Glu Lys Glu Val Glu Ala Ser
145                 150                 155                 160
Val Thr Asn Lys Arg Lys Ala Ala Ala Val Ser Leu Asn Gln Val Lys
                165                 170                 175
```

<210> SEQ ID NO 5
<211> LENGTH: 260
<212> TYPE: PRT
<213> ORGANISM: Acetobacterium woodii

<400> SEQUENCE: 5

Met Asp Thr Phe Leu Lys Leu Pro Val Val Lys Val Asn Gly Asp Gln
1               5                   10                  15

Thr Gln Ile Ile Asp Glu Thr Ile Thr Glu Tyr Pro Leu Thr Leu
            20                  25                  30

Tyr Val Asn Asp Lys Val Phe Asn Thr Phe Tyr Cys Thr Pro Gln Asp
        35                  40                  45

Leu Glu Ala Leu Val Val Gly Tyr Leu Met Ser Cys Gly Arg Leu Gly
    50                  55                  60

Ala Lys Gln Asp Ile Leu Gly Leu Glu Ile Ile Arg Lys Lys Asn Ile
65                  70                  75                  80

Ala Lys Ile Gln Leu Ala Lys Cys Ala Thr Lys Pro Glu Leu Lys Pro
                85                  90                  95

Val Glu Lys Pro Met Leu Val Lys Ile Glu Asn Ile Tyr Glu Ile Met
            100                 105                 110

Ile Lys Asn Ile Lys Pro Thr Glu Leu Phe Leu Lys Thr Gly Gly Phe
        115                 120                 125

His Asn Val Ala Ile Tyr Asp Asn Lys Lys Glu Ile Ile Thr Met Met
    130                 135                 140

Asp Val Ala Arg His Asn Ala Val Asp Lys Val Leu Gly Tyr Cys Val
145                 150                 155                 160

Leu Asn Glu Ile Asp Cys Arg Asp Lys Met Leu Val Val Ser Gly Arg
                165                 170                 175

Ile Ser Val Asp Met Leu Ile Lys Ala Glu Gln Gly Asn Ile Pro Met
            180                 185                 190

Val Leu Ser Lys Ser Ala Pro Thr Ser Leu Ser Val Ala Arg Ala Asp
        195                 200                 205

Ala Ala Gly Ile Thr Leu Val Gly Phe Ile Arg Gly Glu Gln Met Asn
    210                 215                 220

Val Tyr Thr His Pro Thr Arg Ile Asp Leu Gly Glu Glu Ala Phe Arg
225                 230                 235                 240

Ala Ile Asn Lys Asn Lys Arg Ile Thr Ser Met Lys Asn Ala Ser Ile
                245                 250                 255

Tyr Leu Arg Ser
            260

<210> SEQ ID NO 6
<211> LENGTH: 186
<212> TYPE: PRT
<213> ORGANISM: Acetobacterium woodii

<400> SEQUENCE: 6

Met Asn Asn Asn Leu Gly Ser Phe Val Val Ala Cys Asn Asp Gln Cys
1               5                   10                  15

Thr Gly Cys Lys Ala Cys Glu Ile Ala Cys Phe Thr Val His Asn Gln
            20                  25                  30

Lys Glu Asn Lys Val Ala His Thr Val Gly Thr Val Ala Ile Pro Val
        35                  40                  45

Thr Pro Arg Leu Phe Leu Thr Lys Phe Glu Glu Gln Cys Leu Pro Ile
    50                  55                  60

```
Gln Cys Lys Gln Cys Glu Asp Ala Pro Cys Leu Asn Ser Cys Ala Ala
65                  70                  75                  80

Lys Ala Ile Thr Lys Val Asp Gly Thr Met Ile Val Asn Glu Met Leu
                85                  90                  95

Cys Ile Gly Cys Lys Asn Cys Met Leu Ala Cys Pro Phe Gly Ala Ile
            100                 105                 110

Glu Met Leu Pro Ile Ala Lys Asn Ala Gln Pro Val Gln Gln Ile Gly
        115                 120                 125

Ser Asp Glu Val Arg Lys Ser Ala Phe Lys Cys Asp Leu Cys Ala Glu
    130                 135                 140

Leu Glu Asp Gly Pro Ala Cys Val Lys Ala Cys Pro His Asp Val Leu
145                 150                 155                 160

Lys Leu Met Asn Leu Glu Glu Asp Arg Lys Glu Lys Ser Ile Arg Ala
                165                 170                 175

Ala Ile Ala Leu Thr Leu Thr Gly Asn Leu
            180                 185

<210> SEQ ID NO 7
<211> LENGTH: 459
<212> TYPE: PRT
<213> ORGANISM: Acetobacterium woodii

<400> SEQUENCE: 7

Met Ile Ile Asn Ile Asp Lys Glu Ile Cys Thr Gly Cys Arg Glu Cys
1               5                   10                  15

Ala Glu Val Cys Pro Val Ser Ala Ile Glu Gly Glu Pro Gly Lys Gly
                20                  25                  30

Gln Glu Ile Asn Tyr Asp Lys Cys Val Met Cys Gly Gln Cys Val Gln
            35                  40                  45

Lys Cys Lys Ser Tyr Val Ser Ile Val Asp His Gly Val Lys Ala Tyr
    50                  55                  60

Glu Arg Lys Arg Gln Glu Arg Asn Leu Pro Ala Ser Ile Lys Glu Pro
65                  70                  75                  80

Leu Phe Ala Ala Tyr Asn Asn Cys Asn Leu Asp Lys Val Lys Ala Ala
                85                  90                  95

Leu Ala Asp Pro Asp Val Ile Thr Met Val Gln Cys Ala Pro Ala Val
            100                 105                 110

Arg Val Gly Ile Ala Glu Asp Phe Gly Ala Glu Leu Gly Thr Val Ala
        115                 120                 125

Ala Gly Lys Leu Ala Ala Leu His Lys Ile Gly Phe Asp Arg Val
    130                 135                 140

Tyr Asp Thr Asn Phe Thr Ala Asp Leu Thr Ile Met Glu Glu Gly Thr
145                 150                 155                 160

Glu Leu Ile Lys Arg Ile Thr Glu Gly Ala Gly Lys Leu Pro Met Phe
                165                 170                 175

Thr Ser Cys Cys Pro Ala Trp Val Thr Phe Leu Glu Arg Asn Tyr Pro
            180                 185                 190

Asp Gln Lys Asp His Leu Ser Thr Cys Lys Ser Pro Gln Gln Met Gly
        195                 200                 205

Ala Ile Phe Lys Thr Tyr Gly Ala Lys Leu Asp Asn Tyr Asp Pro Ala
    210                 215                 220

Lys Ile Phe Thr Val Ser Val Met Pro Cys Thr Cys Lys Glu Phe Glu
225                 230                 235                 240

Cys Asn Arg Glu Glu Met Asn Ser Ser Gly Tyr Gln Asp Ile Asp Val
```

```
                245                 250                 255
Ala Ile Thr Thr Arg Glu Leu Ala Tyr Leu Ile Lys Asp Met Asp Ile
            260                 265                 270

Asp Phe Asn Ala Leu Ala Asp Glu Asp Phe Asp Gln Pro Leu Gly Glu
        275                 280                 285

Tyr Thr Gly Ala Gly Thr Ile Phe Gly Val Thr Gly Val Met Glu
    290                 295                 300

Ala Ala Ile Arg Thr Gly Tyr Glu Leu Ile Thr Gly Lys Pro Ile Pro
305                 310                 315                 320

Asp Ile Asp Val Ser Ala Val Arg Gly Ser Asn Ala Phe Arg Thr Ala
                325                 330                 335

Thr Leu Lys Val Gly Asp Leu Asp Leu Lys Val Gly Ile Val Thr Gly
            340                 345                 350

Leu Ala Asn Val Ile Pro Val Met Glu Asp Leu Lys Ala Gly Lys Leu
        355                 360                 365

Asp Leu His Phe Ile Glu Val Met Thr Cys Pro Val Gly Cys Val Ser
    370                 375                 380

Gly Gly Gly Gln Pro Lys Leu Leu Asp Ser Glu Lys Glu Ala Ala
385                 390                 395                 400

Tyr Glu Ser Arg Thr Lys Gly Ile Tyr Thr His Asp Ala Glu Leu Pro
                405                 410                 415

Ile Arg Lys Ser His Glu Asn Pro Ala Ile Thr Lys Ile Tyr Glu Glu
            420                 425                 430

Tyr Leu Leu Ser Pro Asn Gly Lys Glu Ser His His Met Leu His Thr
        435                 440                 445

His Tyr Gly Thr Gly Glu Asn Ser Phe Gln Lys
    450                 455

<210> SEQ ID NO 8
<211> LENGTH: 632
<212> TYPE: PRT
<213> ORGANISM: Acetobacterium woodii

<400> SEQUENCE: 8

Met Ser Asn Glu Ile Leu Asn Tyr Asp Lys Val Ala Glu Ala Ser Leu
1               5                   10                  15

Ala Lys Ala Gln Arg Asp Gly Ala Glu Thr Met Trp Asp Arg Arg Ala
            20                  25                  30

Ala Gln Lys Thr Gln Cys Gly Phe Gly Glu Ala Gly Val Cys Cys Arg
        35                  40                  45

Ile Cys Ala Met Gly Pro Cys Arg Val Ser Pro Val Pro Gly Lys Gly
    50                  55                  60

Ala Glu Arg Gly Ile Cys Gly Ala Asn Ala Asp Thr Ile Val Ala Arg
65                  70                  75                  80

Asn Phe Ala Arg Met Val Ala Gly Gly Thr Ser Ala His Ser Asp His
                85                  90                  95

Ala Arg Asp Ile Val His Ala Met His Gly Ala Lys Ala Glu Gly Pro
            100                 105                 110

Phe Lys Ile Arg Asp Glu Ala Lys Leu Arg Arg Ile Ala Gly Glu Trp
        115                 120                 125

Gly Ile Glu Ala Ala Asp Thr Lys Glu Thr Tyr Ala Leu Ala His Glu
    130                 135                 140

Leu Ala Asp Met Ala Leu Gln Glu Phe Gly Lys Pro Phe Gly Thr Gln
145                 150                 155                 160
```

```
Arg Phe Leu Lys Arg Ala Pro Ile Ala Arg Gln Glu Leu Trp Glu Arg
            165                 170                 175

Glu Arg Ile Ala Pro Arg Ala Ile Asp Met Glu Val Thr Thr Leu Met
        180                 185                 190

His Ser Thr His Met Gly Cys Ala Ser Asp Tyr Glu Ser Leu Phe Arg
    195                 200                 205

Arg Gly Met Arg Thr Gly Leu Ser Asp Gly Trp Gly Ser Met Ile
210                 215                 220

Gly Thr Glu Phe Ser Asp Ile Met Tyr Gly Thr Pro Ser Ala Arg Pro
225                 230                 235                 240

Ser Ser Ser Asn Leu Gly Val Ile Asp Ala Glu Met Val Asn Val Leu
                245                 250                 255

Ile His Gly His Asp Pro Asn Leu Ala Glu Met Val Val Leu Ala Ala
            260                 265                 270

Gln Asn Pro Glu Met Val Glu Leu Ala Lys Ala Lys Gly Ala Lys Gly
        275                 280                 285

Ile Asn Ile Val Gly Met Cys Cys Thr Gly Asn Glu Met Thr Met Arg
        290                 295                 300

His Gly Ile Lys Ile Ala Gly Asn Phe Tyr Gln Gln Glu Met Cys Ile
305                 310                 315                 320

Ile Thr Gly Ala Ile Glu Ala Val Val Asp Val Gln Cys Ile Phe
            325                 330                 335

Pro Ala Leu Pro Ala Leu Ala Lys Thr Tyr His Thr Arg Phe Ile Ser
            340                 345                 350

Thr Ser Gln Lys Ala Lys Ile Ser Gly Asp Met Tyr Ile Glu Phe Ser
        355                 360                 365

Glu Glu Thr Gly Leu Glu Asn Ala Asn Glu Ile Ile Lys Ile Ala Val
        370                 375                 380

Glu Asn Phe Pro Asn Arg Asp Ala Ala Lys Val Glu Ile Pro Asp Ile
385                 390                 395                 400

Lys Gln Asp Thr Met Val Gly Tyr Ser Val Glu Ala Ile Ile Asp His
            405                 410                 415

Leu Asp Ala Val Val Asn Ser Gln Leu Glu Asp Glu Leu Gly Thr Val
            420                 425                 430

Lys Pro Leu Thr Asp Val Ile Tyr Ala Gly Val Leu Arg Gly Ala Ala
        435                 440                 445

Gly Val Val Gly Cys Asn Asn Pro Lys Gln Gln His Asp Tyr Ala His
450                 455                 460

Val Lys Val Met Glu Glu Leu Ile Lys Arg Asp Val Ile Cys Val Val
465                 470                 475                 480

Thr Gly Cys Ala Ala Gln Ala Ala Lys Ala Gly Leu Leu Thr Leu
            485                 490                 495

Glu Ala Lys Asp Arg Cys Gly Arg Gly Leu Leu Glu Val Cys Glu Arg
        500                 505                 510

Val Asn Ile Pro Pro Val Leu His Met Gly Ser Cys Val Asp Ile Ser
        515                 520                 525

Arg Ile Leu His Ile Val Asn Leu Cys Ala Asp Val Arg Gly Ile Asp
        530                 535                 540

Pro Ala Leu Leu Pro Val Gly Ile Ala Pro Glu Trp Met Ser Glu
545                 550                 555                 560

Lys Ala Val Ser Ile Ala Asn Tyr Val Val Gly Ser Gly Ile Asn Thr
            565                 570                 575

Tyr Leu Gly Val Ile Pro Gln Val Leu Gly Ser Pro Asn Phe Thr Lys
```

-continued

```
            580                 585                 590
Leu Leu Thr Glu Asp Cys Gln Glu Phe Ile Gly Ala His Phe Val Phe
            595                 600                 605

Glu Lys Asp Pro Ile Val Met Val Asp Lys Ile Met Glu Asp Met Glu
            610                 615                 620

Glu Lys Arg Thr Ala Leu Gly Ile
625                 630
```

METHOD FOR STORING GASEOUS HYDROGEN THROUGH PRODUCING METHANOATE (FORMATE)

CROSS REFERENCE TO RELATED APPLICATIONS

This application is a Divisional Application of co-pending application Ser. No. 14/890,301, filed Nov. 10, 2015; which is the National Stage Application of International Application Number PCT/EP2014/062892, filed Jun. 18, 2014; which claims priority to European Application No. 13172411.4, filed Jun. 18, 2013; all of which are incorporated herein by reference in their entirety.

The Sequence Listing for this application is labeled "SeqList-09Nov15.txt", which was created on Nov. 9, 2015, and is 29 KB. The entire content is incorporated herein by reference in its entirety.

FIELD OF THE INVENTION

The present invention relates to a method for storing gaseous hydrogen, comprising the steps of producing methanoate (formate) through contacting gaseous hydrogen with carbon dioxide in the presence of a hydrogen dependent carbon dioxide reductase (HDCR), and thereby storing of said gaseous hydrogen. The HDCR and/or its complex is preferably derived from *Acetobacterium woodii*.

BACKGROUND OF THE INVENTION

One promising alternative to fossil fuels is hydrogen. Through its reaction with oxygen, hydrogen releases energy explosively in heat engines or quietly in fuel cells to produce water as its only byproduct. Hydrogen is abundant and generously distributed throughout the world without regard for national boundaries. Storing hydrogen in a high-energy-density form that flexibly links its production and eventual use is a key element of the hydrogen economy.

Boddien et al. (in: $CO_2$-"Neutral" Hydrogen Storage Based on Bicarbonates and Formates. Angew. Chem. Int. Ed., 2011 50: 6411-6414) describe a ruthenium catalyst generated in situ that facilitates the selective hydrogenation of bicarbonates and carbonates, as well as $CO_2$ and base, to give formates and also the selective dehydrogenation of formates back to bicarbonates. The two reactions can be coupled, leading to a reversible hydrogen-storage system.

KR 2004/0009875 describes an electrochemical preparation method of formic acid using carbon dioxide, thereby simultaneously carrying out reduction of carbon dioxide and conversion of carbon dioxide into useful organic matters. The method comprises electrochemical reduction of carbon dioxide using formic acid dehydrogenase or formic acid dehydrogenase-producing anaerobic bacteria and an electron carrier in which reversible oxidation/reduction is occurred at electric potential of −400 to −600 mV, wherein the concentration of the electron carrier is 5 to 15 mM; the anaerobic bacteria are selected from *Clostridium thermoaceticum, Clostridium thermoauthotrophicum, Acetobacterium woodii, Acetogenium kivui, Clostridium aceticum, Clostridium ljungdahlii, Eubacterium limosum* or a mixture thereof; the electron carrier is selected from methylviologen, N,N,-diethyl-4,4-bipyridyl, N,N-diisopropylyl-4,4-bipyridyl, 4,4-bipyridyl or a mixture thereof; the reduction temperature is 20 to 70° C.; and the reduction pH is 6.0 to 7.0.

WO 2011/087380 describes methods for improving the efficiency of carbon capture in microbial fermentation of a gaseous substrate comprising CO and/or $H_2$; said method comprising applying an electrical potential across the fermentation. It further relates to improving the efficiency of carbon capture in the microbial fermentation of gaseous substrate comprising CO and/or $H_2$ to produce alcohol(s) and/or acid (s).

Catalytic processes may be used to convert gases consisting primarily of CO and/or CO and hydrogen ($H_2$) into a variety of fuels and chemicals. Microorganisms may also be used to convert these gases into fuels and chemicals. These biological processes, although generally slower than chemical reactions, have several advantages over catalytic processes, including higher specificity, higher yields, lower energy costs and greater resistance to poisoning.

The ability of microorganisms to grow on CO as a sole carbon source was first discovered in 1903. This was later determined to be a property of organisms that use the acetyl coenzyme A (acetyl CoA) biochemical pathway of autotrophic growth (also known as the Wood-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products. The Wood-Ljungdahl pathway of anaerobic $CO_2$ fixation with hydrogen as reductant is considered a candidate for the first life-sustaining pathway on earth because it combines carbon dioxide fixation with the synthesis of ATP via a chemiosmotic mechanism.

Schuchmann et al. (A bacterial electron-bifurcating hydrogenase. J Biol Chem. 2012 Sep. 7; 287(37):31165-71) describe a multimeric [FeFe]-hydrogenase from *A. woodii* containing four subunits (HydABCD) catalyzing hydrogen-based ferredoxin reduction. Apparently, the multimeric hydrogenase of *A. woodii* is a soluble energy-converting hydrogenase that uses electron bifurcation to drive the endergonic ferredoxin reduction by coupling it to the exergonic $NAD^+$ reduction.

Schiel-Bengelsdorf, and Dürre (in:Pathway engineering and synthetic biology using acetogens, FEBS Letters, 2012, 586, 15, 2191) describe acetogenic anaerobic bacteria that synthesize acetyl-CoA from $CO_2$ or CO. Their autotrophic mode of metabolism offers the biotechnological chance to combine use of abundantly available substrates with reduction of greenhouse gases. Several companies have already established pilot and demonstration plants for converting waste gases into ethanol, an important biofuel and a natural product of many acetogens. Recombinant DNA approaches now opened the door to construct acetogens, synthesizing important industrial bulk chemicals and biofuels such as acetone and butanol. Thus, novel microbial production platforms are available that no longer compete with nutritional feedstocks.

WO 2011/028137 describes a bioreactor system for fermentation of a gaseous substrate comprising CO and optionally $H_2$, or $CO_2$ and H2, to one or more products, including acid(s) and/or alcohol(s).

U.S. Pat. No. 7,803,589 describes an *Escherichia coli* microorganism, comprising a genetic modification, wherein said genetic modification comprises transformation of said microorganism with exogenous bacterial nucleic acid molecules encoding the proteins cobalamide corrinoid/iron-sulfur protein, methyltransferase, carbon monoxide dehydrogenase, acetyl-CoA synthase, acetyl-CoA synthase disulfide reductase and hydrogenase, whereby expression of said proteins increases the efficiency of producing acetyl-CoA from $CO_2$, CO or $H_2$, or a combination thereof.

Poehlein et al. (An ancient pathway combining carbon dioxide fixation with the generation and utilization of a sodium ion gradient for ATP synthesis. PLoS One. 2012; 7(3): e33439. doi:10.1371/journal.pone.0033439) describes that the synthesis of acetate from carbon dioxide and molecular hydrogen is considered to be the first carbon assimilation pathway on earth. It combines carbon dioxide fixation into acetyl-CoA with the production of ATP via an energized cell membrane. How the pathway is coupled with the net synthesis of ATP has been an enigma. The anaerobic, acetogenic bacterium *Acetobacterium woodii* uses an ancient version of this pathway without cytochromes and quinones. It generates a sodium ion potential across the cell membrane by the sodium-motive ferredoxin:NAD oxidoreductase (Rnf). The genome sequence of *A. woodii* solves the enigma: it uncovers Rnf as the only ion-motive enzyme coupled to the pathway and unravels a metabolism designed to produce reduced ferredoxin and overcome energetic barriers by virtue of electron-bifurcating, soluble enzymes.

BRIEF SUMMARY

As mentioned above, hydrogen is one of the most discussed future energy sources. Methods for producing hydrogen are well known, but storage and transport of the gas is an unsolved problem. It is therefore an object of the present invention, to provide new and effective methods in order to provide for new ways to store hydrogen, in particular directly from the gaseous phase. Other objects and advantages will become apparent to the person of skill upon studying the following description and the examples of the invention.

BRIEF DESCRIPTION OF THE DRAWINGS

The following figures, sequences, and examples merely serve to illustrate the invention and should not be construed to restrict the scope of the invention to the particular embodiments of the invention described in the examples. For the purposes of the present invention, all references as cited in the text are hereby incorporated in their entireties.

BRIEF DESCRIPTION OF THE SEQUENCES

Sequence ID NOs: 1 to 8 show the amino acid sequences of the enzymes FdhF1, HycB1, FdhF2, HycB2, FdhD, HycB3, HydA2, and AcsA of *A. woodii*, respectively.

DETAILED DESCRIPTION

According to a first aspect thereof, the object of the present invention is solved by providing a method for storing gaseous hydrogen, comprising the steps of producing methanoate (formate) through contacting gaseous hydrogen with carbon dioxide in the presence of a hydrogen dependent carbon dioxide reductase (HDCR), and thereby storing of said gaseous hydrogen.

The present invention is based on the surprising finding that the HDCR enzyme, and preferably a respective enzyme complex, has been found to convert gaseous $H_2+CO_2$ directly into formate in the reaction $H_2+CO_2 \rightarrow HCOOH$. The present biological system functions at normal, such as ambient, pressure and temperature, preferably at standard ambient temperature and pressure or at between about 20° C. to about 40° C. and normal pressure. The method furthermore has a high conversion rate, compared with known chemical catalysts. Also, preferably no additional energy has to be provided.

Since the reaction takes place closely to the thermodynamic equilibrium, in the reverse reaction, hydrogen can be readily released from the formate.

In contrast to the $H_2$ to be converted, the $CO_2$ can be provided in the method both in gaseous and/or solid from. Preferred is a method of the present invention, wherein the $CO_2$ is provided in the form of hydrogen carbonate ($HCO3^-$) (see also FIG. 3).

Preferred is a method according to the present invention, wherein the method does not involve electrochemical reduction, in particular of carbon dioxide. No electric energy has to be provided, and in particular no means for providing an electrical potential to a bioreactor as involved.

Preferred is a method according to the present invention, wherein said HDCR is selected from a bacterial enzyme, such as, for example FdhF1 (Ace. No. YP_005268500, SEQ ID No.1) or FdhF2 (Acc. No. YP 005268502, SEQ ID No.2) of *Acetobacterium woodii*.

Also preferred are formate dehydrogenase enzymes that are at least 65% identical to the FdhF1 and/or FdhF2 enzyme, more preferably at least 70%, even more preferred at least 80%, and most preferred at least 90% identical to the FdhF1 and/or FdhF2 enzyme on the amino acid level. Preferred examples are selected from the formate dehydrogenase-H of *Clostridium difficile* 630 (Acc. No. YP_001089834.2), the formate dehydrogenase h of *Clostridium difficile* CD196 (Acc. No. YP_003216147.1), the formate dehydrogenase of *Clostridium* sp. DL-VIII (Acc. No. WP_009172363.1), the formate dehydrogenase of *Clostridium arbusti* (Acc. No. WP_010238540.1), the formate dehydrogenase of *Clostridium ragsdalei* (Acc. No. gb|AEI90724.1), the formate dehydrogenase H of *Paenibacillus polymyxa* E681 (Acc. No. YP_003871035.1), the formate dehydrogenase-H of *Clostridium difficile* 630 (Acc. No. YP_001089834.2), the formate dehydrogenase h of *Clostridium difficile* CD196 (Acc. No. YP_003216147.1), the formate dehydrogenase H of *Treponema primitia* ZAS-2 (Ace. No. ADJ19611.1), the formate dehydrogenase H of *Clostridium carboxidivorans* P7 (Acc. No. AD012080.1), and the formate dehydrogenase I of *Clostridium ragsdalei* (Ace. No. gb|AEI90722.1), and mixtures thereof. All these proteins shall be understood as "homologs" of the proteins of *Acetobacterium woodii* as described herein.

Further preferred is a method according to the present invention, wherein said HDCR is part of an enzyme complex, for example with a formate dehydrogenase accessory protein, such as, for example, FdhD of *Acetobacterium*

*woodii*, an electron transfer protein, such as, for example, HycB1 or HycB2 of *Acetobacterium woodii*, and a subunit harboring the active site characteristic of an [FeFe]-hydrogenase, such as, for example, HydA2 of *Acetobacterium woodii*. Also preferred are formate dehydrogenase accessory proteins and/or electron transfer proteins and/or [FeFe]-hydrogenase proteins, that are at least 65% identical to the HydA2, FdhD, HycB1 and/or HycB2 enzyme, more preferably at least 70%, even more preferred at least 80%, and most preferred at least 90% identical to the HydA2, FdhD, HycB1 and/or HycB2 enzyme on the amino acid level, and show an electron transfer activity, formate dehydrogenase accessory protein activity, or [FeFe]-hydrogenase activity. Also these proteins shall be understood as "homologs" of the proteins of *Acetobacterium woodii* as described herein.

Particularly preferred is a method according to the present invention, wherein said HDCR is part of the enzyme complex comprising FdhF1/2, HycB1/2/3, and HydA2. Thereby, FdhF reduces $CO_2$ to formate, the electrons are provided by HydA2, the subunit of the $H_2$-oxidation. More preferably the HDCR is a protein complex composed of the subunits FdhF1/FdhF2, HycB1/HycB2, HydA2 and HycB3. Most preferably the HDCR is selected from one of the complexes comprising FdhF1, HycB1, HydA2 and HycB3, or the complex comprising FdhF2, HycB2, HydA2 and HycB3

Further preferred is a method according to the present invention, wherein said method further comprises an inhibition of the cellular metabolism to further metabolize formate, such as an Na depletion, for example using sodium ionophores. When the metabolism of the cell is inhibited (and/or impaired), the formate as produced can no longer react further, and is advantageously produced as the final product. For the inhibition of the energy metabolism, all substances can be used that are known to the person of skill, and examples are selected from all ATPase inhibitors, such as DCCD (dicyclohexylcarbodiimide), heavy metals such as silver ions, copper ions, etc., all decoupling agents of the membrane potential, such as protonophores such as TCS (3,3',4',5-tetrachlorosalicylanilide), K-ionophores, such as valinomycine, propyl iodide as inhibitor of cobalt dependent reactions, phosphate starvation, which slows down ATP-synthesis, and tensides or substances that destroy the integrity of the membrane of the cell. It is important, that an enzyme and/or step of the energy metabolism is blocked, since this leads to an accumulation of the intermediate product. Since the HDCR is independent from the energy metabolism and does not require external electron carriers or energy, the process of formate formation can continue. This phenomenon can of course be applied both to reactions in whole cells, as well as in in vitro-reactions. The inventors have furthermore surprisingly found that the synthesis of acetyl-CoA can be stopped at formate, if Na is depleted. The system (for example bacteria) then nearly exclusively produces formate, which is used for hydrogen storage. Depletion can be achieved by using sodium-free buffers and/or media, and/or by using sodium-ionophores, such as, for example, Monensin, Gramicidin A, or the commercially available ETH 2120 (N,N,N',N'-Tetracyclohexyl-1,2-phenylenedioxydiacetamide, Selectophore™), or the like.

In another aspect of the present invention the present invention thus is based on the surprising finding that the inhibition of the cellular metabolism to further metabolize formate, such as by Na depletion (for example using sodium ionophores) can be advantageously used toproduce foiinate. In this embodiment, the Na depletion leads to an accumulation of formate based on the effective blocking of the production of downstream products from the formate.

The present invention thus further relates to a method for producing methanoate (formate) comprising contacting carbon dioxide in the presence of a hydrogen dependent carbon dioxide reductase (HDCR) under conditions that inhibit the cellular metabolism to further metabolize formate, such as, for example, under Na depletion, at an electric potential of −300 to −600 mV (e.g. using electrodes) and/or in the presence of an electron carrier. The concentration of the electron carrier can be from 5 to 15 mM, and the electron carrier can be selected from methylviologen, N,N,-diethyl-4,4-bipyridyl, N,N-diisopropylyl-4,4-bipyridyl, 4,4-bipyridyl or a mixture thereof. Preferably, said HDCR is selected from a bacterial enzyme, such as, for example FdhF1 or FdhF2 of *Acetobacterium woodii*. More preferably the HDCR is a protein complex composed of at least one of the subunits FdhF1/FdhF2, HycB1/HycB2, HydA2 and HycB3. Most preferably the HDCR is selected from one of the complexes comprising FdhF1, HycB1, HydA2 and HycB3, or the complex comprising FdhF2, HycB2, HydA2 and HycB3. Further preferably, said method is performed under standard ambient temperature and pressure, or at between about 20° C. to about 40° C. and normal pressure. Other preferred embodiments of this method are analogous as described herein for the first aspect of the present invention.

Yet another aspect of the present invention then relates to a method according to the present invention, further comprising the step of converting carbon monoxide into carbon dioxide using a CO dehydrogenase, such as, for example a bacterial CO dehydrogenase, such as, for example AcsA of *Acetobacterium woodii*, and a ferredoxin. Also preferred are CO dehydrogenase enzymes that are at least 65% identical to the AcsA enzyme, more preferably at least 70%, even more preferred at least 80%, and most preferred at least 90% identical to the AcsA enzyme on the amino acid level, and show a CO dehydrogenase activity. All these proteins shall be understood as "homologs" of the proteins of *Acetobacterium woodii* as described herein.

In this aspect of the present invention, it was furthermore surprisingly found that the enzyme hydrogen dependent carbon dioxide reductase (HDCR) can also use carbon monoxide (via ferredoxin) as electron donor for the $CO_2$-reduction to formate. Thus, this enables the advantageous use of synthesis gas (for example as feed-stock) for the method. Of course, this aspect of the invention also can be performed under the conditions and using the complex and enzymes as described above for the "direct" $CO_2$-use. Furthermore, this aspect of the method of the invention can be used to remove CO from gaseous phases, and thus can constitute a method for decontaminating CO-contaminated (or polluted) gases.

Yet another aspect of the present invention thus relates to a method for decontaminating CO-contaminated or polluted gases, comprising performing a method according to the invention as above using said CO-contaminated or polluted gas as a substrate. Preferably, said CO-contaminated or polluted gas is synthesis gas.

In the methods according to the present invention, both purified (or partially purified) enzyme(s) as well as bacterial cells can be used. Thus, methods according to the present invention can be performed in vitro, in vivo and/or in culture, for example in imidazole buffer (see below).

Most preferred is a method according to the present invention, which is performed in a bioreactor in a continuous operation or in batches. Respective methods and devices are known to the person of skill and described (for example, in Demler and Weuster-Botz; Reaction engineering analysis of hydrogenotrophic production of acetic acid by *Acetobacterium woodii*. Biotechnol Bioeng. 2011 February; 108(2): 470-4).

Yet another aspect of the present invention thus relates to a recombinant bacterial organism comprising a genetic modification, wherein said genetic modification comprises transformation of said microorganism with exogenous bacterial nucleic acid molecules encoding the proteins FdhF1 and/or FdhF2, FdhD, HycB1 and/or HycB2, HydA2, and optionally HycB3 or AcsA of *Acetobacterium woodii*, or homologs thereof as described herein, whereby expression of said proteins increases the efficiency of producing format from $CO_2$, and/or CO and $H_2$. More preferably the nucleic acids encode at least one of the HDCR subunits FdhF1/FdhF2, HycB1/HycB2, HydA2 and HycB3. Most preferably the nucleic acids encode the proteins FdhF1, HycB1, HydA2 and HycB3, or the proteins FdhF2, HycB2, HydA2 and HycB3.

Further preferred is a method according to the present invention, further comprising the (recombinant) expression of the genes of hydrogenase maturation as well as for a cofactor biosynthesis of the formate-dehydrogenase (e.g. described in Kuchenreuther J M, Grady-Smith C S, Bingham A S, George S J, Cramer S P, et al. (2010) High-Yield Expression of Heterologous [FeFe] Hydrogenases in *Escherichia coli*. PLoS ONE 5(11): e15491. doi:10.1371/journal.pone.0015491).

Preferred is the use of the recombinant bacterial organism according to the present invention in a method according to the present invention as described herein.

Yet another aspect of the present invention relates to the use of a hydrogen dependent carbon dioxide reductase (HDCR), for example a bacterial enzyme, such as, for example FdhF1 or FdhF2 of *Acetobacterium woodii* or homologs thereof in a method according to the present invention as described herein. Preferred is a use, wherein said HDCR is part of an enzyme complex, for example with a formate dehydrogenase accessory protein, such as, for example, FdhD of *Acetobacterium woodii*, an electron transfer protein, such as, for example, HycB1 or HycB2 of *Acetobacterium woodii*, and a subunit harboring the active site characteristic of an [FeFe]-hydrogenase, such as, for example, HydA2 of *Acetobacterium woodii*, or homologs thereof. Further preferred is a use according to the present invention, wherein said complex further comprises a CO dehydrogenase, such as, for example a bacterial CO dehydrogenase, such as, for example AcsA of *Acetobacterium woodii*, and a ferredoxin, or homologs thereof. More preferably the HDCR is a protein complex composed of at least one of the subunits FdhF1/FdhF2, HycB1/HycB2, HydA2 and HycB3. Most preferably the HDCR is selected from one of the complexes comprising FdhF1, HycB1, HydA2 and HycB3, or the complex comprising FdhF2, HycB2, HydA2 and HycB3.

Examples

Measurements with the Isolated HCDR

For the purification of HCDR *A.woodii* (DSM 1030) was grown at 30° C. under anaerobic conditions in 20-1-liter flasks using 20 mM fructose to an $OD_{600}$ of ~2.5. All buffers used for preparation of cell extracts and purification contained 2 mM DTE and 4 µM resazurin. All purification steps were performed under strictly anaerobic conditions at room temperature in an anaerobic chamber filled with 100% $N_2$ and 2-5% $H_2$. The cell free extract was prepared as descirbed previously (Schuchmann et al., J Biol Chem. 2012 Sep. 7; 287(37):31165-71). Membranes were removed by centrifugation at 130000 g for 40 minutes. Part of the supernatant containing the cytoplasmic fraction with approximately 1600 mg protein was used for the further purification. Ammonium sulfate (0.4 M) was added to the cytoplasmic fraction. Half of this sample was loaded onto a Phenyl-Sepharose high performance column (1.6 cm×10 cm) equilibrated with buffer A (25 mM Tris/HCl, 20 mM $MgSO_4$, 0.4 M $(NH_4)_2SO_4$, 20% glycerol, pH 7.5). Methylviologen-dependent formate dehydrogenase activity elutet around 0.33 M $(NH_4)_2SO_4$ in a linear gradient of 120 ml from 0.4 M to 0 M $(NH_4)_2SO_4$. This step was repeated with the second half of the sample in a separate run to gain more protein since otherwise large amounts of the activity eluted in the flowthrough. The pooled fractions of both runs were diluted to a conductivity of below 10 mS/cm with buffer C (25 mM Tris/HCl, 20 mM $MgSO_4$, 20% glycerol, pH 7.5) and applied to a Q-Sepharose high performance column (2.6 cm×5 cm) equilibrated with buffer C. Protein was eluted with a linear gradient of 160 ml from 150 mM to 500 mM NaCl. Formate dehydrogenase eluted at around 360 mM NaCl. Pooled fractions were concentrated using ultrafiltration in 100-kDa VIASPIN tubes and applied to a Superose 6 10/300 GL prepacked column equilibrated with buffer C and eluted at a flow rate of 0.5 ml/min. Formate dehydrogenase activity eluted as a single peak. Pooled fractions were stored at 4° C. Measurements of HCDR activity were performed at 30° C. with in buffer 1 (100 mM HEPES/NaOH, 2 mM DTE, pH 7.0) in 1.8 ml anaerobic cuvettes sealed by rubber stoppers, containing 1 ml buffer and a gas phase of $0.8×10^5$ Pa $H_2$ and $0.2×10^5$ $CO_2$. Production of formate was measured using Formate dehydrogenase of *Candida boidinii* with 2 mM NAD in the assay and production of NADH was followed.

For measurements with ferredoxin as electron carrier Ferredoxin was purified from *Clostridium pasteurianurn*. For reduction of ferredoxin CO dehydrogenase of *A. woodii* was purified and in these experiments the gas phase of the cuvettes was changed to 100% CO ($1.1×10^5$ Pa).

Whole Cells

Figure 1A:
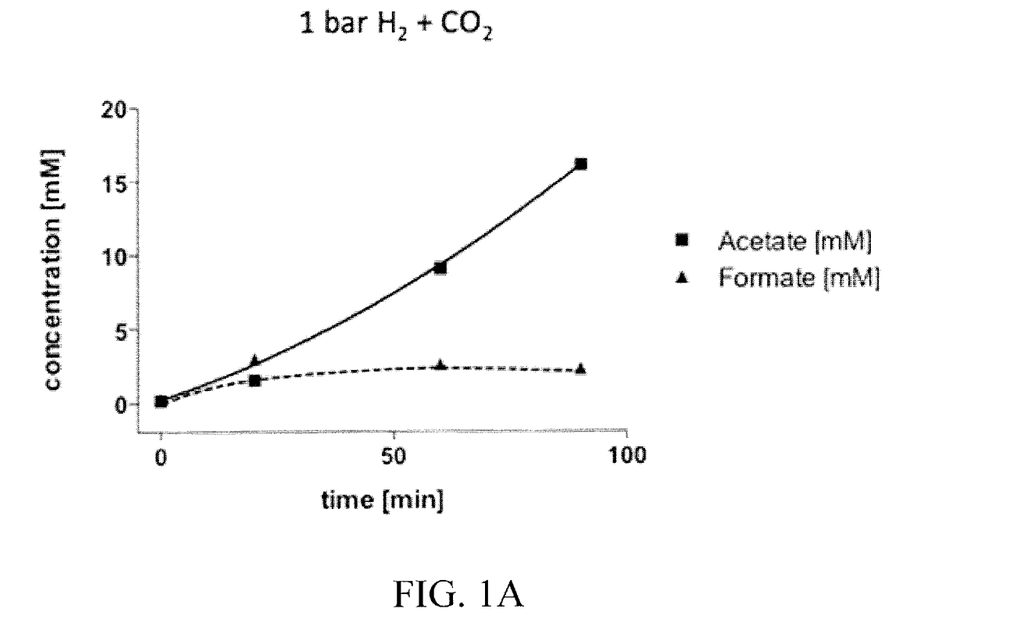
FIGS. 1A-1B shows the productions of formate using whole cell catalysis. Cell suspensions of *A. woodii* (1 mg/ml) were incubated using a gas phase of $0.8 \times 10^5$ Pa $H_2$ and $0.2 \times 10^5$ Pa $CO_2$ (1A). Adding the $Na^+$ ionophore ETH2120 (30 µM) gives rise to the production of up to 8 mM formate and the production of acetate stopped (1B).
Figure 1B:
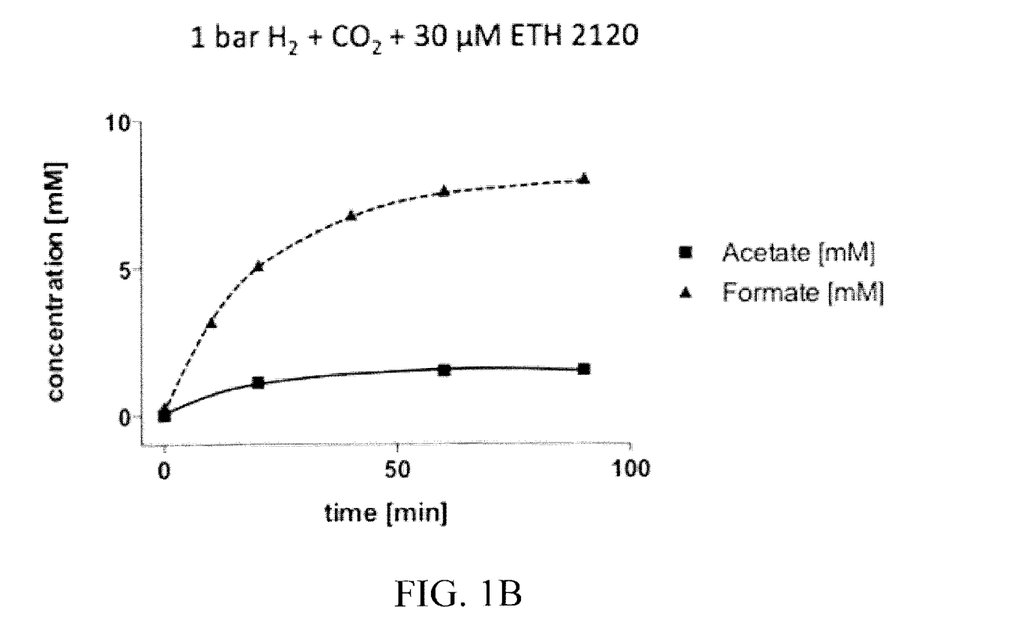

For experiments with whole cells, the inventors used cell suspensions of *A. woodii* for the conversion of $H_2$ and $CO_2$ to formate. The energy metabolism of *A. woodii* is strictly sodium ion dependent, and the ATP synthase uses $Na^+$ as the coupling ion. Thus, by omitting sodium ions in the buffer or by adding sodium ionophores (the inventors used the ionophore ETH2120 in this study), it is possible to switch off the energy metabolism specifically. Cells suspended in imidazole buffer (50 mM imidazole, 20 mM $MgSO_4$, 20 mM KCl, 4 mM DTE, pH 7.0) containing 20 mM NaCl converted $H_2+CO_2$ to acetate, and only small amounts of formate were produced from a gas phase of $0.8×10^5$ Pa $H_2$ and $0.2×10^5$ $CO_2$. By adding ETH2120 (30 µM), acetate production ceased almost completely and formate was produced with an initial rate of 2 µmol/min×mg cell protein (FIG. 1). In agreement with the results obtained from the purified enzyme, formate production was also observed when hydrogen was absent and the electron donor was CO but with lower rates compared to hydrogen as electron donor.

Figure 2:
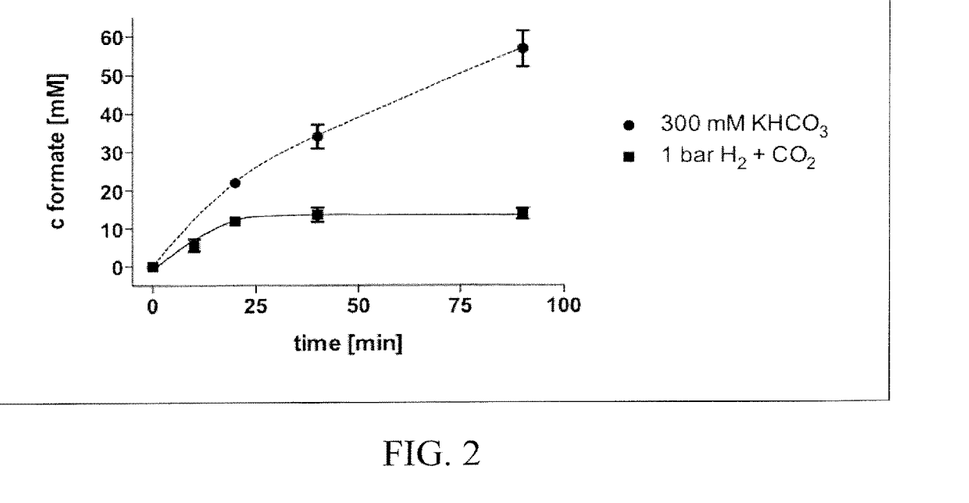
FIG. 2 shows the production of formate using $HCO_3^-$ or $CO_2$ as substrate. Cell suspensions of *A. woodii* (1 mg/ml) were incubated using a gas phase of $0.8 \times 10^5$ Pa $H_2$ and $0.2 \times 10^5$ Pa $CO_2$ or $1 \times 10^5$ Pa $H_2$ with 300 mM $KHCO_3$.

The results in FIG. 1 demonstrate that a maximal amount of around 8 mM of formate was produced in this experiment. The inventors next tested, if the final formate concentration is proportional to the initial gas pressure. From 0.5 to $2×10^5$ Pa $H_2+CO_2$ the final formate concentration did not increase. Since the inventors observed a pH drop during the experiment, the inventors examined if the lower pH is the limiting factor. Increasing the buffer concentration from 50 to 200 mM resulted in a final formate concentration of around 14±3 mM. If $CO_2$ was exchanged with $KHCO_3$ the effect was even more dramatic. By using the base $HCO_3^-$ the overall process is almost pH neutral compared to the production of formic acid from $CO_2$. The genome of *A. woodii* encodes for a carboanhydrase that allows the rapid interconversion of $CO_2$ and $HCO_3^-$. FIG. 2 shows the production of formate from initially 300 mM $KHCO_3$ (with $1\times10^5$ Pa $H_2$) compared to $CO_2$ as substrate. Finally up to 184±5 mM formate were produced with $KHCO_3$.

Figure 3:
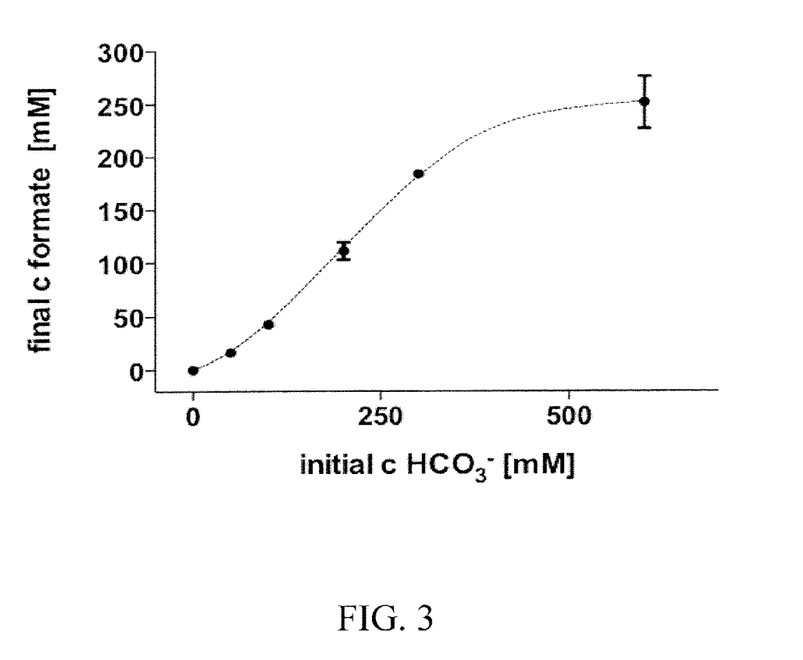
FIG. 3 shows the relationship of final formate concentration to initial $HCO_3^-$. Cell suspensions of *A. woodii* (1 mg/ml) were incubated with increasing amounts of initial $HCO_3^-$ and a gas phase of $1 \times 10^5$ Pa $H_2$.

The relationship of the final formate concentration to the initial concentration of $HCO_3^-$ is shown in FIG. 3. Up to 300 mM $HCO_3^-$, the final formate concentration increases with increasing substrate concentration. Furthermore the final formate concentration fits well to the theoretic thermodynamic limit of the reaction underlining the independence of the carboxylation of $CO_2/HCO_3^-$ from other cellular processes. At $1\times10^5$ Pa $H_2$, the thermodynamic equilibrium is approximately $[HCO_3^-]=[HCOOH]$, so equimolar concentrations of substrate and product. At concentrations of $HCO_3^-$ above 300 mM, this relationship does not exist anymore and the final amount of formate produced ceased around 300 mM.

The invention claimed is:

1. A recombinant bacterial organism comprising a genetic modification, wherein said genetic modification comprises transformation of said microorganism with exogenous bacterial nucleic acid molecules encoding the proteins;
 i) FdhF1 and/or FdhF2,
 ii) FdhD,
 iii) HycB1 and/or HycB2,
 iv) HydA2, and
 v) HycB3,
 or homologs thereof,
 whereby expression of said proteins increases the efficiency of producing formate from $CO_2$, and/or CO and $H_2$.

2. The recombinant bacterial organism according to claim 1, wherein said FdhD protein is FdhD of *Acetobacterium woodii* or, a homolog thereof.

3. The recombinant bacterial organism according to claim 1, wherein said organism further comprises nucleic acid molecules encoding, a CO dehydrogenase and a ferredoxin, or a homolog thereof.

4. The recombinant bacterial organism according to claim 3, wherein said CO dehydrogenase is AcsA of *Acetobacterium woodii*, or a homolog thereof.

5. The recombinant bacterial organism according to claim 1, wherein said HycB1 and/or HycB2 proteins are HycB1 and/or HycB2 of *Acetobacterium woodii*, or a homolog thereof.

6. The recombinant bacterial organism according to claim 1, wherein said HydA2 protein is HydA2 of *Acetobacterium woodii*, or a homolog thereof.

7. The recombinant bacterial organism according to claim 1, comprising nucleic acid molecules encoding FdhF1, FdhD, HycB1, HydA2 and HycB3.

8. The recombinant bacterial organism according to claim 1, comprising nucleic acid molecules encoding FdhF2, FdhD, HycB1, HydA2 and HycB3.

9. The recombinant bacterial organism according to claim 1, comprising nucleic acid molecules encoding FdhF1, FdhD, HycB2, HydA2 and HycB3.

10. The recombinant bacterial organism according to claim 1, comprising nucleic acid molecules encoding FdhF2, FdhD, HycB2, HydA2 and HycB3.

11. The recombinant bacterial organism according to claim 1, comprising nucleic acid molecules encoding FdhF1, FdhF2, FdhD, HycB1, HydA2 and HycB3.

12. The recombinant bacterial organism according to claim 1, comprising nucleic acid molecules encoding FdhF1, FdhF2, FdhD, HycB2, HydA2 and HycB3.

13. The recombinant bacterial organism according to claim 1, comprising nucleic acid molecules encoding FdhF2, FdhD, HycB1, HycB2, HydA2 and HycB3.

14. The recombinant bacterial organism according to claim 1, comprising nucleic acid molecules encoding FdhF1, FdhD, HycB1, HycB2, HydA2 and HycB3.

15. The recombinant bacterial organism according to claim 1, comprising nucleic acid molecules encoding FdhF1, FdhF2, FdhD, HycB1, HycB2, HydA2 and HycB3.

* * * * *